United States Patent [19]

Kamishita

[11] Patent Number: 4,670,254

[45] Date of Patent: * Jun. 2, 1987

[54] GEL PREPARATIONS FOR TOPICAL APPLICATION OF DICLOFENAC SODIUM

[75] Inventor: Takuzo Kamishita, Takatsuki, Japan

[73] Assignee: Toko Yakuhin Industry Co., Ltd., Osaka, Japan

[*] Notice: The portion of the term of this patent subsequent to Sep. 24, 2002 has been disclaimed.

[21] Appl. No.: 779,519

[22] Filed: Sep. 24, 1985

Related U.S. Application Data

[63] Continuation-in-part of Ser. No. 559,730, Dec. 9, 1983, Pat. No. 4,543,251.

[51] Int. Cl.$^4$ .................................................. A61K 31/78
[52] U.S. Cl. ....................................................... 424/81
[58] Field of Search ........................................... 424/81

[56] References Cited

U.S. PATENT DOCUMENTS 3,749,773  7/1973  Ninger et al. ................... 424/81
4,309,414  1/1982  Inagi et al. ...................... 424/81
4,407,824  10/1983  Eckert ............................ 424/329

*Primary Examiner*—Stanley J. Friedman
*Attorney, Agent, or Firm*—Stiefel, Gross, Kurland & Pavane

[57] ABSTRACT

Anti-inflammatory, stable and painless topical gel preparations comprising diclofenac sodium as the active ingredient; water, ethanol and a glycol as the solvent medium; a carboxyvinyl polymer obtained by the polymerization of acrylic acid as a gelling agent; and a weakly basic aliphatic amine as a neutralizing agent for the carboxyvinyl polymer.

7 Claims, 5 Drawing Figures

GEL PREPARATIONS FOR TOPICAL APPLICATION OF DICLOFENAC SODIUM

CROSS-REFERENCE TO RELATED APPLICATION

This application is a continuation-in-part of application Ser. No. 559,730 filed Dec. 9, 1983, now U.S. Pat. No. 4,543,251 granted Sept. 24, 1985.

BACKGROUND OF THE INVENTION

1. Field of the Invention

The present invention relates to stable, painless gel preparations for the topical application of diclofenac sodium.

2. Description of the Prior Art

Diclofenac sodium is a derivative of phenylacetic acid, having the formula

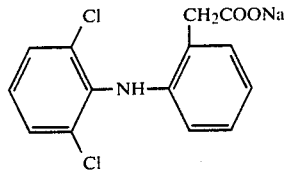

Diclofenac sodium is a non-steroid drug soluble in water and alcohols, and having excellent anti-inflammatory and analgetic effects. At the present time, it is used only in the form of oral preparations or suppositories exhibiting excellent anti-inflammatory and analgetic effects when so administered. However, side effects such as stomach and intestine problems, liver problems and kidney problems, may occur, especially upon oral administration. Therefore, anti-inflammatory and analgetic preparations which are absorbed cutaneously without showing such side effects are desired.

In this regard, a gel preparation for topical application containing indomethacin, a non-steroidal anti-inflammatory, is known (Japanese Patent Laid-open No. Sho 53(1978)-81616). However, this preparation is unstable, and possesses a yellow color (the color of indomethacin) which soils clothes.

Accordingly, it is among the objects of the present invention to provide topical formulations containing diclofenac sodium which are stable, which may be readily employed without pain or other side effects, and which do not soil clothing or have other undesirable characteristics.

SUMMARY OF THE INVENTION

The present invention provides gel preparations for topical application containing from about 1.0 to 3.0 percent by weight of diclofenac sodium as the active ingredient; a medium comprising water, ethanol and a glycol selected from among ethylene glycol, propylene glycol and 1,3-butylene glycol in an amount at least sufficient to dissolve the diclofenac sodium, the medium containing less than about 40 percent by weight ethanol and less than about 30 percent by weight of the glycol and the ratio of water to the combination of ethanol and the glycol being from about 7:3 to 5:5 by weight; a gelling agent comprising a hydrophilic carboxyvinyl polymer obtained by the polymerization of acrylic acid; and an aliphatic amine neutralizing agent in an amount sufficient to adjust the pH of the preparation to about 6.7–7.7. Diclofenac sodium gel preparations so constituted have good stability, are readily applied without any discomfort, and exhibit excellent cutaneous absorptive characteristics insuring the desired anti-inflammatory and analgetic effects.

DESCRIPTION OF THE PREFERRED EMBODIMENTS

Figure 1:
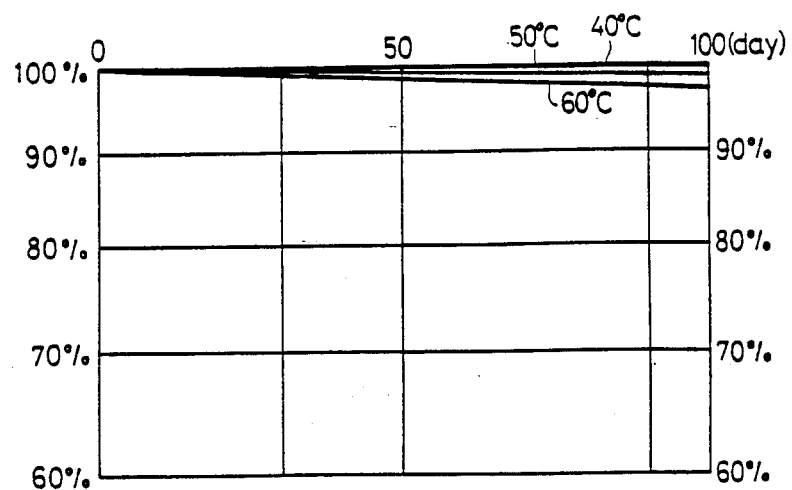
FIG. 1 is a graph showing the stability with time of diclofenac sodium contained in the preparation of Example 1 of the present invention.
Figure 2:
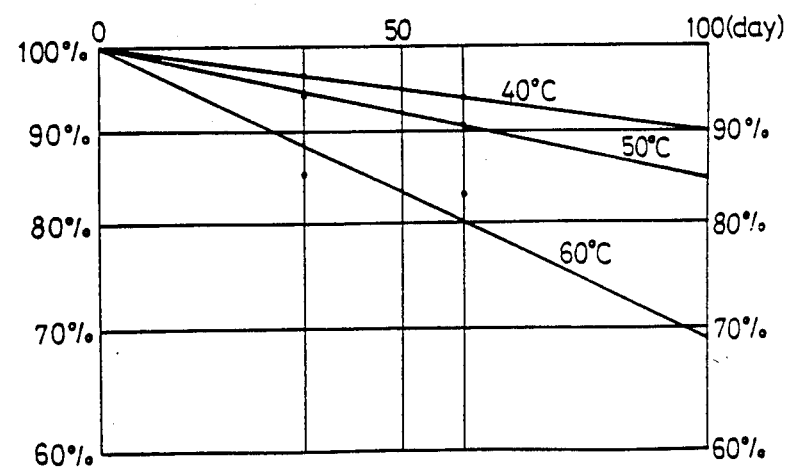
FIGS. 2 to 5 are graphs showing the stability with time of diclofenac sodium contained in the preparations of Controls A–D below, respectively.
Figure 3:
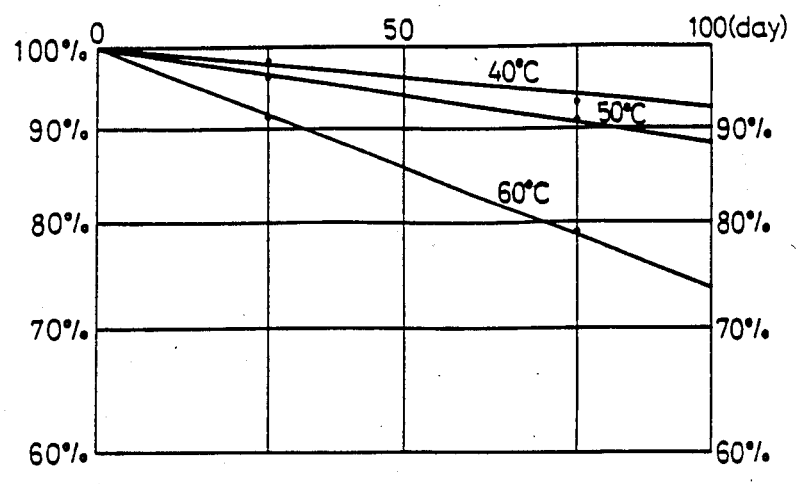
Figure 4:
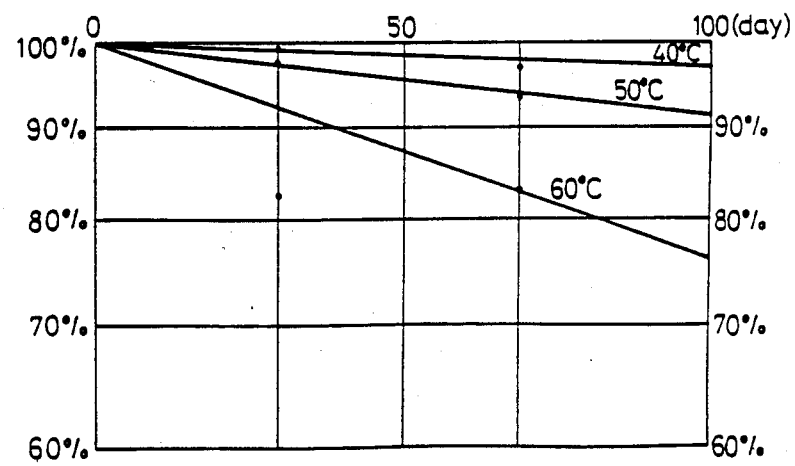
Figure 5:
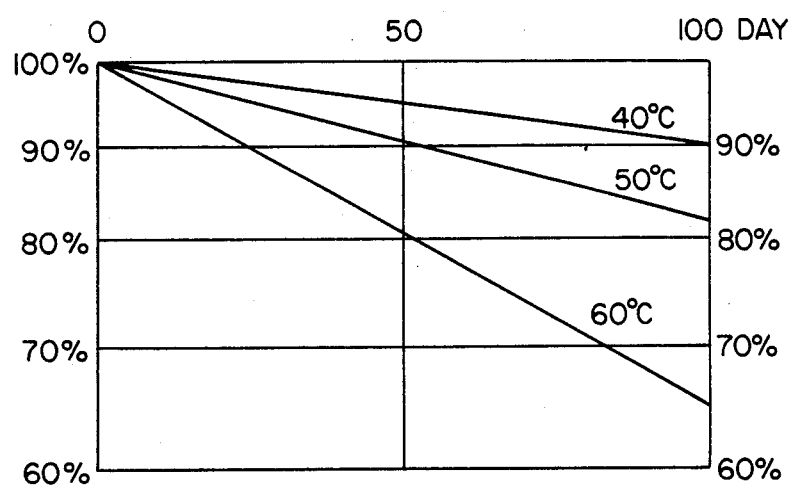

Diclofenac sodium, the active ingredient, is incorporated in the gel preparations of the present invention in an amount of from about 1.0 to 3.0 percent by weight, preferably from about 1.0 to 2.0 percent by weight.

As indicated hereinabove, the medium for the active ingredient comprises a mixture of water, ethanol and ethylene glycol, propylene glycol or 1,3-butylene glycol. It is possible to prepare a stable gel preparation of diclofenac sodium using as a medium a mixture of water with only ethanol or another lower alkanol, or a mixture of water with soley a glycol. However, when only water and a lower alkanol are used, absorption of the diclofenac sodium is poor, since the preparation dries so easily that the diclofenac sodium crystallizes out on the surfce of the skin. On the other hand, when a mixture of water and a glycol are used as the medium, it is necessary to use the glycol in an amount of at least 30 percent in order to dissolve dichlofenac sodium sufficiently. However, when a glycol is used in the gel in an amount of 30 percent or more, the preparation does not dry well on the skin. Moreover, skin irritation due to an excess amount of glycol remains a problem.

When, on the oter hand, the medium contains both water, ethanol (or another low alkanol) and the glycol, but the medium incorporates 40 percent or more of the ethanol or 30 percent or greater quantities of the glycol, the preparation is subject to other disadvantages. Thus, such formulations may be subject to resinification of the carboxyvinyl polymer, liquefaction of the gel and/or precipitation of the diclofenac sodium. The preferred gel preparations of the present invention are so constituted as to avoid these problems.

The weight ratio of water to organic solvents in the medium varies, as noted hereinabove, from about 7:3 to 5:5. Preferred preparations suitably contain water:ethanol:the glycols in approximately 60:30:10 parts by weight. Most desirably, the medium contains water, ethanol and propylene gylcol, or water, ethanol and 1,3-butylene glycol, in the indicated proportions.

The carboxyvinyl polymer used as the gelling agent in the present preparations is a hydrophilic polymer obtained by the polymerization of acrylic acid as the principal component. Preferably, the carboxyvinyl polymer is a copolymer of an alpha, beta-unsaturated carboxylic acid, viz., acrylic acid, and a polyalkenylpolyether of a polyhydric alcohol (including polyalkenylpolyethers of oligosaccharides containing at least two allyl ether groups). Such materials are described, for example, in Goodrich Japanese published Patent Application No. 4141/1957 filed on Jan. 14, 1954, the disclosure of which is incorporated by this reference herein. Suitable commercially available carboxyvinyl polymers include Hiviswako 103, Hiviswako 104, and Hiviswako 105 from Wakojunyakukogyo K.K. of Japan, and Carbopol 934, Carbopol 940 and Carbopol 941 from Goodrich Chemical Co. of the U.S.A., or the like.

In accordance with the invention, the carboxyvinyl polymer is neutralized with a neutralizing agent which cross-links and gelatinizes the polymer. When preparations containing such materials contact the skin, they are readily decomposed by salt or the like, forming solutions from which the diclofenac sodium is readily absorbed into the skin. By proper formulation of the carboxyvinyl polymer and the neutralizing agent, the preparations thus provide excellent absorptive characteristics in addition to superior stability and ease of application.

In the present preparations, a weakly basic, aliphatic amine is used as the neutralizing agent in an amount sufficient to adjust the pH almost to neutrality, that is, to a pH of about 6.7 to 7.7. An amount of, for example, about 1.5–3.0 percent by weight of the aliphatic amine is sufficient for this purpose. Aliphatic amines which may be so utilized include primary, secondary, or tertiary alkanolamines or alkylamines, such as monoethanolamine, diethanolamine, diisopropanolamine, triethanolamine, or triisopropanolamine; or dimethylamine, diethylamine, trimethylamine or triethylamine. Especially preferred among these are triethanolamine and diisopropanolamine.

Use of such a weak basic substance as the neutralizing agent is one of the characteristic features of the present invention. Use of a strong base such as sodium hydroxide as the neutralizing agent is inappropriate. In the free acid form carboxyvinyl polymers are more strongly acidic than diclofenac. However, carboxyvinyl polymers are by themselves weak acids. Accordingly, when a strong base such as sodium hydroxide is used as the neutralizing agent, the pH value increases to about 9. While a gel preparation of diclofenac sodium may be prepared under these conditions, the use of such a relatively alkaline formulation is undesirable since it causes skin irritation.

On the oter hand, when diclofenac sodium gel preparations are prepared without neutralizing the carboxyvinyl polymer, the free acid of diclofenac is formed. Although the diclofenac sodium salt is stable, the free acid itself is only barely soluble and loses stability upon aging.

If desired, an auxiliary agent comprising peppermint oil, l-menthol, methyl salicylate, ethyl salicylate or glycol monosalicylate, either separately or in admixture, may be added to the gel preparations of the invention. Peppermint oil and l-menthol impart a cool feeling to the skin, and salicylic acid derivatives accelerate cutaneous absorption of the active ingredient. The auxiliary agent is applied as an inductive stimulant, and increases the analgetic effects; it is suitably incorporated in an amount of from about 0.5 to 5 percent by weight of the preparations.

Other additives known in the art, such as aromatic agents, antiseptics, colorants, or the like may also be added in small amounts to the preparations, if desired. Usually, however, the addition of such further additives is not necessary.

The gel preparations of the invention can be prepared, for example, by initially dissolving diclofenac sodium in ethanol. To the solution thus obtained is added an aqueous solution of a carboxyvinyl polymer and the glycol, with stirring. The neutralizing agent is then added to the solution, with stirring, in an amount sufficient to adjust the pH of the resulting gel preparation to about 6.7–7.7. Alternatively, the gel preparations can be prepared by adding an aqueous solution of the carboxyvinyl polymer to a solution obtained by dissolving diclofenac sodium in a mixture of ethanol and the glycol, with stirring, and the adding the neutralizing agent to the solution with continued stirring.

The gel preparations hereof have good stability. They do not show any substantial changes in viscosity at high temperatures or crystallization at low temperatures. Moreover, they adhere well to the skin and spread quite readily. Further, they do not impart a sticky feeling and dry easily.

The following examples illustrate preferred embodiments of the diclofenac sodium-containing topical gel preparations of the present invention, and contrast the characteristics thereof with the properties of various control formulations. Unless otherwise indicated, all parts and precentages specified in the examples are given by weight.

EXAMPLE 1

Diclofenac sodium (1 g) was dissolved in 95% ethanol (30 g) with stirring. Propylene glycol (10 g), a 4% aqueous solution (25 g) of a carboxyvinyl polymer (Carbopol 940), and purified water (20 g), were separately and uniformly mixed, and triethanolamine (1.5 g) was thereafter added to the mixture with continued stirring. The previously prepared alcoholic solution of diclofenac sodium was then added to the gel base, and the volume of the mixture was adjusted to 100 g by the further addition of purified water. After stirring well, a gel preparation having a viscosity of 20,000 centipoises and a pH of 7.15 was obtained.

EXAMPLE 2

A further gel preparation was prepared in the same manner as described in Example 1, containing the following ingredients:

| COMPONENT | AMOUNT |
| --- | --- |
| Diclofenac sodium | 2.0 g |
| 95% ethanol | 30.0 g |
| Propylene glycol | 10.0 g |
| Carbopol 940 (4% aqueous solution) | 30.0 g |
| Triethanolamine | 2.0 g |
| Water | 26.0 g |
| Total | 100.0 g |

CONTROL A

Diclofenac sodium (1.0 g) and peppermint oil (3.0 g) were dissolved in 95% ethanol (40 g) by stirring. Separately, a 3% solution (20 g) of Carbopol 940 in propylene glycol, and a 4% aqueous solution (25 g) of Carbopol 940, citric acid (0.3 g) and purified water (8.0 g) were uniformly mixed by stirring; triethanolamine (0.05 g) was added thereto with continued stirring to produce the desired gel base. The alcoholic solution of diclofenac sodium and peppermint oil was added to the gel base, and the mixture was adjusted to 100 g by the further addition of purified water. After stirring, a gel preparation having a viscosity of 22,000 centipoises and a pH of 5.2 was obtained.

CONTROL B

Diclofenac sodium (1.0 g) was dissolved in 95% ethanol (40 g) by stirring. Separately, a 3% solution (20 g) of Carbopol 940 in propylene glycol, and a 4% aqueous solution (25 g) of Carbopol 940 and purified water (10 g) were uniformly mixed together b stirring; triethanolamine (0.05 g) was thereafter added to the mixture while continuing the stirring. The alcoholic solution of diclofenac sodium was added to the resulting gel base and the mixture was adjusted to 100 g by the further additon of purified water. After stirring, a gel preparation having a viscosity of 23,000 centipoises and a pH of 5.4 was obtained.

CONTROL C

Diclofenac sodium (1.0 g) was dissolved in 95% ethanol (20 g) by stirring. Separately, a 3% solution (40 g) of Carbopol 940 in propylene glycol, and a 4% aqueous solution (10 g) of Carbopol 940 and purified water (25 g) were uniformly mixed by stirring, and triethanolamine (0.8 g) was added to the mixture while continuing the stirring. The alcoholic solution of diclofenac sodium was added and the mixture was adjusted to 100 g by the further addition of purified water. After stirring, a gel preparation having a viscosity of 21,000 centipoises and a pH of 5.8 was obtained.

CONTROL D

An ointment of the below composition was prepared by the same method as described in Example 1.

| | |
|---|---|
| Carboxyvinyl polymer | 1.0 (g) |
| Indomethacin | 1.0 |
| Propylene glycol | 10.0 |
| Ethanol | 40.0 |
| Diisopropanol amine | 1.1 |
| Purified water | As amount sufficient to bring the final weight to 100 g |

Viscosity: 18500 cp
pH: 6.5

STABILITY TESTS

The stability of the diclofenac sodium in the gel preparation of Example 1 was compared with its stability in Conrols A, B, C, and D. In particular, the diclofenac sodium content in each preparation was measured just after formation of the prepartion and after the lapse of prescribed periods, by extracting the diclofenac sodium withe ethanol, isolating the diclofenac sodium from the extract by HPLC (column: Lichrosorb $RP_{18}$, developing agent: methanol/water/acetic acid—600:400:5, room temperature), and determining the ultraviolet absorbance (254 nm).

The loss of diclofenac sodium from the preparation of Example 1 upon aging is shown in FIG. 1, and the losses from the preparations of Controls A, B, C and D are shown in FIGS. 2 to 5, respectively (abscissa: days elapsed, ordinate: percentages of the active ingredient in the preparation, that just after formation of the preparation being taken as 100%). It is apparent that the preparation of Example 1 has significantly greater stability with time, as compared with the preparations of the several controls.

ANTI-INFLAMMATORY TESTS

The anti-inflammatory characteristics of the topical preparations of Examples 1 and 2 were evaluated against carrageenin edema in rats. The test preparations were compared with the control formulations identified below:

TABLE I

| | Test Preparations | | | |
|---|---|---|---|---|
| Ingredient | Ex. 1 (1% DF gel) | Ex. 2 (2% DF gel) | Control E (0.5% DF gel) | Control F (placebo) |
| diclofenac sodium (DF) | 1.0 | 2.0 | 0.5 | — |
| 95% ethanol | 30.0 | 30.0 | 30.0 | 30.0 |
| propylene glycol | 10.0 | 10.0 | 10.0 | 10.0 |
| Carbopol 940 (4% aqueous solution) | 25.0 | 30.0 | 25.0 | 30.0 |
| triethanolamine | 1.5 | 2.0 | 1.5 | 2.0 |
| water | 32.5 | 26.0 | 33.0 | 26.0 |
| TOTAL | 100.0 | 100.0 | 100.0 | 98.0 |

There further control preparations (1) an indomethacin gel (Control D) containing 1% indomethacin; (2) a Mobilat ointment (Control G) containing 0.2% of a heparin-like substance, 1% adrenal extract and 2% salicylic acid (commercially available from Maruho KK of Japan) were also tested for comparative anti-inflammatory properties. The following results were obtained:

TABLE II

COMPARATIVE ANTI-INFLAMMATORY CHARACTERISTICS OF TOPICAL PREPARATIONS ON PAW EDEMA INDUCED BY CARRAGEENIN IN RATS

| | | After Carrageenin Injection | | | |
|---|---|---|---|---|---|
| | | 3 Hr. | | 5 Hrs. | |
| | N | Swelling % Mean ±S.E. | Inhibitory % | Swelling % Mean ±S.E. | Inhibitory % |
| Example 1 | 12 | 43.1 ± 3.8** | 27.7 | 45.9 ±2.7* | 16.5 |
| Example 2 | 12 | 36.6 ± 1.4** | 38.6 | 35.7 ± 1.7** | 35.1 |
| Control E | 12 | 49.8 ± 2.8** | 16.4 | 49.7 ± 3.7 | 9.6 |
| Control F | 11 | 59.6 ± 1.7 | — | 55.0 ± 2.2 | — |
| Control D | 11 | 41.4 ± 2.** | 30.5 | 37.8 ± 2.5** | 31.3 |

*$P < 0.05$
**$P < 0.01$
Test ointment (100 mg) was applied 1 and 2 hrs. before carrageenin injection. Effect was measured 3 and 5 hrs. after carrageenin injection.
N: The number of tested rats
"Inhibitory %" means
$$\frac{\text{The value of swelling of Control F} - \text{that of other sample}}{\text{The value of swelling of Control F}} \times 100$$

TABLE III

COMPARATIVE EFFECTS OF TOPICAL PREPARATION ON CARRAGEENIN EDEMA IN RATS

| | N | Dose (mg/site × 2) | Edema Volume (ml, Mean ± S.D.) | | | |
|---|---|---|---|---|---|---|
| | | | 1 hr | 2 hrs | 3 hrs | 4 hrs |
| Example 2 | 13 | 100 | 0.29 ± 0.12 | 0.45 ± 0.13* | 0.52 ± 0.10*** | 0.66 ± 0.11*** |
| Control F | 13 | — | 0.29 ± 0.08 | 0.58 ± 0.10 | 0.70 ± 0.10 | 0.94 ± 0.18 |
| Control D | 13 | 100 | 0.29 ± 0.09 | 0.52 ± 0.10 | 0.57 ± 0.08** | 0.78 ± 0.13* |

TABLE III-continued

| COMPARATIVE EFFECTS OF TOPICAL PREPARATION ON CARRAGEENIN EDEMA IN RATS | | | | | |
|---|---|---|---|---|---|
| | | Dose | Edema Volume (ml, Mean ± S.D.) | | |
| | N | (mg/site × 2) | 1 hr | 2 hrs | 3 hrs | 4 hrs |
| Control G | 13 | 100 | 0.18 ± 0.08** | 0.50 ± 0.15 | 0.61 ± 0.13 | 0.84 ± 0.20 |

Significant difference from control:
*$P < 0.05$
**$P < 0.01$
***$P < 0.001$, respectively.
N: the number of tested rats From the preceding it may be seen that the topical preparations of the present invention exhibit markedly superior anti-inflammatory characteristics, i.e., edema inhibition, as compared with the various control formulations.

SUPPLEMENTAL STABILITY TESTS

The relationship between gel stability and various of the parameters of the diclofenac sodium topical preparations is indicated in Tables IV and V. In particular, the tables indicate gel characteristics upon variation of the proportions of the media components, the identity of the alkanol constituent, gel pH, etc:

TABLE IV

| DICLOFENAC SODIUM GEL CHARACTERISTICS WITH CHANGES IN GEL COMPOSITION | | | | | | | |
|---|---|---|---|---|---|---|---|
| | Gel Composition (% by weight) | | | | | | |
| DF—Na[1] | Alkanol | PG[2] | CVP[3] | TEA[4] | H$_2$O | pH | |
| 1.0 | 30(EtOH) | 10 | 1.2 | 0.5 (NaOH) | to 100 | 7.0 | resinification of CVP and liquefaction |
| 2.0 | 30 (isopropanol) | 10 | 1.2 | 2.0 | " | 7.1 | resinification of CVP and liquefaction |
| 2.0 | 30(EtOH) | 10 | 1.2 | 1.5 | " | 6.3 | resinification of CVP and precipitation of DF—Na crystals |
| 2.0 | 45(EtOH) | 5 | 1.2 | 2.0 | " | 7.2 | resinification of CVP and liquefaction |
| 2.0 | 10(EtOH) | 40 | 1.2 | 2.0 | " | 7.2 | precipitation of DF—Na crystals after several days |
| 2.0 | 20 (isopropanol) | 20 | 2.0 | 3.0 | " | 7.2 | resinification of CVP and liquefaction |
| 3.0 | 20 (isopropanol) | 20 | 2.0 | 3.0 | " | 7.2 | resinification of CVP and liquefaction |
| 3.5 | 30(EtOH) | 10 | 1.2 | 2.0 | " | 7.2 | resinification of CVP and liquefaction |
| 5.0 | 20 (isopropanol) | 20 | 2.0 | 3.0 | " | 7.2 | resinification of CVP and liquefaction |

TABLE V

| DICLOFENAC SODIUM GEL CHARACTERISTICS WITH CHANGES IN RATIOS OF MEDIA COMPONENTS | | | | | |
|---|---|---|---|---|---|
| Ratio of Water: Organic Components in Medium | Water | Organic Medium | | Gel Characteristics DF—Na | |
| | | EtOH | PG | 2% | 1% |
| 5:5 | 50 | 50 | 0 | X | O |
| | 50 | 40 | 10 | O | O |
| | 50 | 30 | 20 | O | O |
| | 50 | 20 | 30 | O | O |
| | 50 | 10 | 40 | X | X |
| | 50 | 0 | 0 | X | X |
| 6:4 | 60 | 40 | 0 | O | O |
| | 60 | 30 | 10 | O | O |
| | 60 | 20 | 20 | O | O |
| | 60 | 10 | 30 | X | |
| | 60 | 0 | 40 | X | X |
| 7:3 | 70 | 30 | 0 | O | O |
| | 70 | 20 | 10 | X | O |
| | 70 | 10 | 20 | X | X |
| | 70 | 0 | 30 | X | X |

X indicates precipitation of diclofenac sodium, or resinification of the carboxyvinyl polymer from the gel.
O indicates that the above precipitation and resinification do not occur.

It will be understood that various changes may be made in the preferred embodiments described hereinabove without departing from the scope of the present invention. Accordingly, the preceding description should be interpreted as illustrative only and not construed in a limiting sense.

I claim:

1. A gel preparation for topical application, which comprises:
   (a) from 1.0% to 3.0% by weight of diclofenac sodium as the active ingredient;
   (b) a medium in an amount at least sufficient to dissolve the active ingredient, comprising water, ethanol, a glycol selected from the group consisting of ethylene glycol, propylene glycol and 1,3-butylene glycol, the weight ratio of water:ethanol:glycol in the medium being about 60:30:10;
   (c) a gelling agent comprising a carboxyvinyl polymer selected from the group consisting of the hydrophilic polymers obtained by polymerization of acrylic acid; and (d) a neutralizing agent comprising an aliphatic amine in an amount sufficient to adjust the pH of the preparation almost to neutrality.

2. The preparation of claim 1, wherein the aliphatic amine is a primary, secondary or tertiary alkanolamine or alkylamine.

3. The preparation of claim 2, wherein the aliphatic amine is triethanolamine or diisopropanolamine.

4. The preparation of claim 1, wherein the carboxyvinyl polymer is a copolymer of acrylic acid and a polyalkenylpolyether of a polyhydric alcohol.

5. The preparation of claim 1, additionally containing peppermint oil, l-menthol or a salicylic acid ester as an auxiliary agent.

6. The preparation of claim 5, wherein the salicylic acid ester is methyl salicylate, ethyl salicylate or glycol salicylate.

7. The preparation of claim 1, incorporating the diclofenac sodium in the amount of 1% by weight thereof.

* * * * *